United States Patent
Thiagarajan et al.

(10) Patent No.: US 9,710,916 B2
(45) Date of Patent: Jul. 18, 2017

(54) KERNEL SPARSE MODELS FOR AUTOMATED TUMOR SEGMENTATION

(71) Applicants: Jayaraman Jayaraman Thiagarajan, Dublin, CA (US); Karthikeyan Ramamurthy, Yorktown Heights, NY (US); Andreas Spanias, Tempe, AZ (US); David Frakes, Scottsdale, AZ (US)

(72) Inventors: Jayaraman Jayaraman Thiagarajan, Dublin, CA (US); Karthikeyan Ramamurthy, Yorktown Heights, NY (US); Andreas Spanias, Tempe, AZ (US); David Frakes, Scottsdale, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 14/853,617

(22) Filed: Sep. 14, 2015

(65) Prior Publication Data
US 2016/0005183 A1 Jan. 7, 2016

Related U.S. Application Data

(63) Continuation of application No. PCT/US2014/028237, filed on Mar. 14, 2014.
(Continued)

(51) Int. Cl.
*G06K 9/00* (2006.01)
*G06T 7/00* (2017.01)
(Continued)

(52) U.S. Cl.
CPC ............ *G06T 7/0081* (2013.01); *A61B 5/055* (2013.01); *G06T 7/0012* (2013.01); *G06T 7/11* (2017.01);
(Continued)

(58) Field of Classification Search
None
See application file for complete search history.

(56) References Cited

U.S. PATENT DOCUMENTS

2005/0197980 A1* 9/2005 Dundar ............... G06K 9/6256
706/16
2006/0093197 A1 5/2006 Unal et al.
(Continued)

FOREIGN PATENT DOCUMENTS

CN 102799870 11/2012

OTHER PUBLICATIONS

Han, Ju, et al. "Comparison of sparse coding and kernel methods for histopathological classification of gliobastoma multiforme." 2011 IEEE International Symposium on Biomedical Imaging: From Nano to Macro. IEEE, 2011.*
(Continued)

*Primary Examiner* — Hadi Akhavannik
(74) *Attorney, Agent, or Firm* — Bryan Cave LLP

(57) ABSTRACT

A robust method to automatically segment and identify tumor regions in medical images is extremely valuable for clinical diagnosis and disease modeling. In various embodiments, an efficient algorithm uses sparse models in feature spaces to identify pixels belonging to tumorous regions. By fusing both intensity and spatial location information of the pixels, this technique can automatically localize tumor regions without user intervention. Using a few expert-segmented training images, a sparse coding-based classifier is learned. For a new test image, the sparse code obtained
(Continued)

from every pixel is tested with the classifier to determine if it belongs to a tumor region. Particular embodiments also provide a highly accurate, low-complexity procedure for cases when the user can provide an initial estimate of the tumor in a test image.

20 Claims, 9 Drawing Sheets

Related U.S. Application Data

(60) Provisional application No. 61/786,292, filed on Mar. 14, 2013.

(51) Int. Cl.
  *A61B 5/055* (2006.01)
  *G06T 7/11* (2017.01)

(52) U.S. Cl.
  CPC ............... *A61B 2576/026* (2013.01); *G06T 2207/10088* (2013.01); *G06T 2207/20081* (2013.01); *G06T 2207/30096* (2013.01)

(56) References Cited

U.S. PATENT DOCUMENTS

| | | | |
|---|---|---|---|
| 2010/0027865 A1* | 2/2010 | Wels | G06K 9/4614 382/131 |
| 2011/0123095 A1 | 5/2011 | Florin et al. | |
| 2012/0093381 A1 | 4/2012 | Fan et al. | |

OTHER PUBLICATIONS

Lin, Yen-Yu, Tyng-Luh Liu, and Chiou-Shann Fuh. "Local ensemble kernel learning for object category recognition." 2007 IEEE Conference on Computer Vision and Pattern Recognition. IEEE, 2007.*

International Search Report and Written Opinion for co-pending International Application No. PCT/US14/28237, Jul. 30, 2014 Jul. 30, 2014.

Aharon, M., Elad, M., and Bruckstein, A., K-SVD: An Algorithm for Designing Overcomplete Dictionaries for Sparse Representation, IEEE Transactions on Signal Processing, vol. 54, No. 11, pp. 4311-4322 Nov. 1, 2006.

Ahmed, M.N., et al., A Modified Fuzzy C-Means Algorithm for Bias Field Estimation and Segmentation of MRI Data, IEEE Transactions on Medical Imaging, vol. 21, No. 3, pp. 193-199 Mar. 1, 2002.

Chan, T.F., and Vese, L.A., Active Contours Without Edges, IEEE Transactions on Image Processing, vol. 10, No. 2, pp. 266-277 Feb. 1, 2001.

Clark, M.C., et al., Automatic Tumor Segmentation Using Knowledge-Based Techniques, IEEE Transactions on Medical Imaging, vol. 17, No. 2, pp. 187-201 Apr. 1, 1998.

Corso, J.J., et al., Efficient Multilevel Brain Tumor Segmentation With Integrated Bayesian Model Classification, IEEE Transactions on Medical Imaging, vol. 27, No. 5, pp. 629-640 May 1, 2008.

Donoho, D.L., Compressed Sensing, IEEE Transactions on Information Theory, vol. 52, No. 4, pp. 1289-1306 Apr. 1, 2006.

Elad, M., and Aharon, M., Image Denoising Via Sparse and Redundant Representations Over Learned Dictionaries, IEEE Transactions on Image Processing, vol. 15, No. 12, pp. 3736-3745 Dec. 1, 2006.

Hamamci, A., et al., Tumor-Cut: Segmentation of Brain Tumors on Contrast Enhanced MR Images for Radiosurgery Applications, IEEE Transactions on Medical Imaging, vol. 31, No. 3, pp. 790-804 Mar. 1, 2012.

Ho, S., Built, E., and Gerig, G., Level-Set Evolution With Region Competition: Automatic 3-D Segmentation of Brain Tumors, Proceedings of the Conference on Pattern Recognition, IEEE, 2002, pp. 532-535 Jan. 1, 2002.

Kaus, Dr. M.R., et al., Automated Segmentation of MR Images of Brain Tumors, Radiology, vol. 218, N. 2, pp. 586-591 Feb. 1, 2001.

Lee, C.H., et al., Segmenting Brain Tumors With Conditional Random Fields and Support Vector Machines, Computer Vision for Biomedical Image Applications, pp. 469-478 2005.

Moon, N., et al., Model-Based Brain and Tumor Segmentation, Proceedings of 16th International Conference on Pattern Recognition, IEEE, pp. 528-531 2002.

Olshausen, B.A., and Field, D.J., Sparse Coding with an Overcomplete Basis Set: A Strategy Employed by V1?, Vision Reg., vol. 37, No. 23, pp. 3311-3325 1997.

Prastawa, M., et al., Automatic Brain Tumor Segmentation by Subject Specific Modification of Atlas Priors, Academic Radiology, vol. 10, No. 12, pp. 1341-1348 Dec. 2003.

Prastawa, M., et al., A brain tumor segmentation framework based on outlier detection, Medical Image Analysis, vol. 8, pp. 275-283 Jul. 17, 2004.

Thiagarajan, J.J., et al., Automated Tumor Segmentation using Kernel Sparse Representations, IEEE 12th International Conference on Bioinformatics & Bioengineering, pp. 401-406 2012.

Thiagarajan, J.J., et al., Kernel Sparse Models for Automated Tumor Segmentation, International Journal on Artificial Intelligence Tools, WSPC Instruction File Mar. 12, 2013.

Thiagarajan, J.J., et al., Multiple Kernel Sparse Representations for Supervised and Unsupervised Learning, IEEE Transactions on Image Processing, vol. 23, No. 7, pp. 2905-2915 Jul. 2014.

Wright, J., et al., Robust Face Recognition via Sparse Representation, IEEE Transactions on Pattern Analysis and Machine Intelligence, vol. 31, No. 2, pp. 210-227 Feb. 2009.

Yu, K., Zhang, T., and Gong, Y., Nonlinear Learning using Local Coordinate Coding, Advances in neural Inforamtion Processing Systesms, vol. 22 2009.

Zibulevsky, M., and Pearlmutter, B.A., Blind Source Separation by Sparse Decomposition in a Signal Dictionary, Neural Computation 13, pp. 863-882 2001.

Thiagarajan, J.J., Ramamurthy, K.N., and Spanias, A., Multilevel Dictionary Learning for Sparse Representation of Images, Proceedings of IEEE DSP Workshop, pp. 271-276 2011.

Chen, S.S., Donoho, D.L., and Saunders, M.A., Atomic Composition by Basis Pursuit, Society for Industrial and Applied Mathematics, vol. 43, No. 1, pp. 129-159 2001.

Lee, H., Battle A., Raina, R., and Ng, A.Y., Efficient Sparse Coding Algorithms, Advances in Neural Information Processing Systems 2007.

Efron, B., Hastie, T., Johnstone, I., and Tibshirani, R., Least Angle Regression, The Annals of Statistics, vol. 32, No. 2, pp. 407-499 2004.

Rubinstein, R., Bruckstein, A.M., Elad, M., Dictionaries for Sparse Representation Modeling, Proceedings of the IEEE, vol. 98, No. 6, pp. 1045-1057 Jun. 2010.

Gao,S., Tsang, I., and Chia, L.T., Kernel Sparse Representation for Image Classification and Face Recognition, Proceedings of ECCV, pp. 1-14 2010.

Ramirez, I., Sprechmann, P., and Sapiro, G., Classification and Clustering Via Dictionary Learning With Structured Incoherence and Shared Features, Proceedings of IEEE CVPR, pp. 3501-3508 2010.

Thiagarajan, J.J., Ramamurthy, K.N., and Spanias, A., Optimally and Stability of the K-Hyperline Clustering Algorithm, Pattern Recognition Letter, vol. 32, pp. 1299-1304 2011.

Nguyen, H.V., et al., Kernel Dictionary learning, Proceedings of the IEEE ICASSP May 10, 2012.

Kwok, J.T. and Tsang, L.W.., The Pre-Image Problem in Kernel Methods, Proceedings of the Twentieth International Conference on Machine Learning 2003.

Ng, A.Y, Jordan, M.I., and Weiss, Y., On Spectral Clustering: Analysis and an Algorithm, Advances in Neural Information Processing Systems, vol. 2, pp. 849-856 2002.

\* cited by examiner (a) (b) (c) (d) (e)

KERNEL SPARSE MODELS FOR AUTOMATED TUMOR SEGMENTATION

CROSS-REFERENCE TO RELATED APPLICATIONS

This application is a continuation application of International Application No. PCT/US14/28237, filed Mar. 14, 2014, which claims priority to U.S. Provisional Application No. 61/786,292, filed Mar. 14, 2013. The entirety of the above-referenced disclosures is specifically incorporated herein by reference without disclaimer.

TECHNICAL FIELD

This disclosure relates to systems and methods for tumor segmentation.

BACKGROUND

Brain tumor detection and segmentation have been of interest to researchers, however, no robust, automated algorithm has been adopted in the clinical setting. Tumors may be malignant or benign as determined by a biopsy, and are known to affect brain symmetry and cause damage to the surrounding brain tissues. In particular, Glioblastoma Multiforme (GBM) is a very common and dangerous malignant primary brain tumor, for example. These tumors are characterized by jagged boundaries with a ring enhancement, possibly a dark core necrotic component, and are accompanied by edema (swelling).

Automated approaches to segment these types of tumors can be challenged by the variability in size, shape and location of the tumor, the high degree of similarity in the pixel intensities between normal and abnormal brain tissue regions, and the intensity variations among identical tissues across volumes. As a result, unsupervised thresholding techniques have not been very successful in accurate tumor segmentation. Furthermore, approaches that incorporate prior knowledge of the normal brain from atlases require accurate non-rigid registration, and hence, generating adequate segmentation results potentially calls for user-intervention and/or a patient specific training system. In addition, these methods can require elaborate preprocessing, and they tend to overestimate the tumor volume. The Chan-Vese active contour method is a widely adopted approach that is usually combined with a level-set evolution for convergence to a region of interest. Though this method is robust to noise in the image, and can work reasonably well even with blurred images, it requires a reliable initial estimate to be provided by the user. Furthermore, the high computational cost of this method preempts its use in a large-scale setting.

BRIEF DESCRIPTION OF THE DRAWINGS

To facilitate further description of the embodiments, the following drawings are provided in which.

Figure 1:
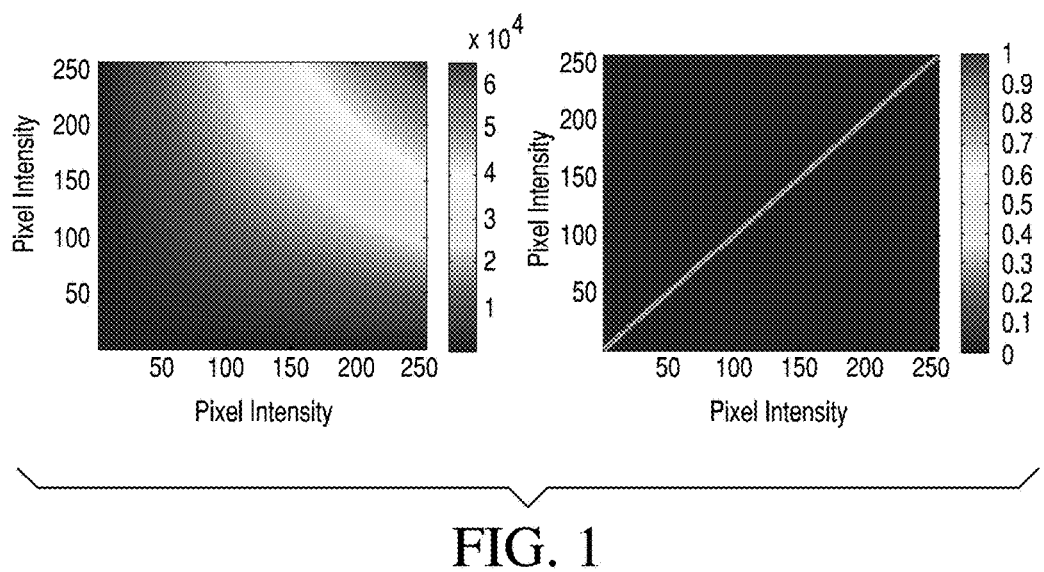
FIG. 1 shows linear similarity (left), and shows non-linear similarity using a Radial Basis Function kernel (right)

For simplicity and clarity of illustration, the drawing figures herein illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types. The absence of the word "removably," "removable," and the like near the word "coupled," and the like does not mean that the coupling, etc. in question is or is not removable.

DESCRIPTION OF EXAMPLES OF EMBODIMENTS

Various embodiments include a method of segmenting a tumor region in an image. The method can be implemented via execution of computer instructions configured to run at one or more processing modules and configured to be stored at one or more non-transitory memory storage modules. The method can include computing a kernel sparse code for each pixel of at least a portion of the image. The method also can include identifying, using a classifier, each pixel belonging to the tumor region.

Several embodiments include a system for segmenting a tumor region in an image. The system can include one or more processing modules and one or more non-transitory memory storage modules storing computing instructions. The computing instruction can be configured to run on the one or more processing modules and perform the certain acts. The computing instructions can perform the act of computing a kernel sparse code for each pixel of at least a portion of the image. The computing instructions also can perform the act of identifying, using a classifier, each pixel belonging to the tumor region.

In various embodiments, an approach to automatically segment enhancing/active and necrotic tumor components from T1-weighted contrast-enhanced magnetic resonance (MR) images is proposed. The segmentation technique described, in a number of embodiments, works without user intervention, and at a moderate computational cost. Each pixel in the image can be represented as a sparse code in a non-linear feature space, for example, taking into account both its intensity and spatial location. Since expert-segmented training images that have clearly marked tumor regions are available, the segmentation problems can be performed using pixel classification. Though the computational complexity of the automated segmentation algorithm can be comparable to several existing methods, in some embodiments, the complexity can be significantly reduced by allowing the user to initialize the tumor region.

Sparse coding-based approaches are proposed for segmentation of tumors from MR images, for example. Sparse coding with data-adapted dictionaries has been successfully employed in several image recovery and vision problems. Since it can be trivial to obtain sparse codes for pixel values, and combining multiple features in the sparse coding setup is not straightforward, we propose to consider their non-linear similarities to perform kernel sparse coding in a high-dimensional feature space. We develop the kernel dictionary learning algorithms (e.g., kernel K-lines clustering) procedure for inferring kernel dictionaries, and use the kernel sparse codes to determine if a pixel belongs to a tumorous region. Note that, in a number of embodiments, this approach can be completely automated, and does not require user intervention to initialize the tumor regions in an image. Furthermore, a low complexity segmentation approach, which allows the user to initialize the tumor region, is also presented. Results show that both of the proposed approaches can lead to accurate tumor identification with a low false positive rate, when compared, for example, to manual segmentation by an expert radiologist.

A robust method to automatically segment a medical image into its constituent heterogeneous regions can be an extremely valuable tool for clinical diagnosis and disease modeling. Given a reasonably large data set, performing manual segmentation is not a practical approach. Brain tumor detection and segmentation, for example, have been of interest to researchers over recent years and previously, there existed no comprehensive algorithm built and adopted in the clinical setting. Although patient scans can be obtained using different imaging modalities, Magnetic Resonance Imaging (MRI) has been used for brain imaging over other modalities because of its non-invasive and non-ionizing nature, and because it allows for direct multi-plane imaging.

Tumors may be malignant or benign as determined by a biopsy, and are known to affect brain symmetry and cause damage to the surrounding brain tissues. Automated tumor segmentation approaches are often challenged by the variability in size, shape and location of the tumor, the high degree of similarity in the pixel intensities between normal and abnormal brain tissue regions, and the intensity variations among identical tissues across volumes. As a result, unsupervised thresholding techniques have not been very successful in accurate tumor segmentation. Furthermore, approaches that incorporate prior knowledge of the normal brain from atlases require accurate non-rigid registration, and hence, generating adequate segmentation results potentially calls for user-intervention and/or a patient specific training system. In addition, these methods require elaborate pre-processing and they tend to over-estimate the tumor volume.

Approaches for tumor segmentation can be either region-based or pixel-based. The active contours method is a widely adopted region-based approach that is usually combined with a level-set evolution for convergence to a region of interest. However, it is sensitive to the contour initialization, and has a high computational cost due to its iterative nature. Model-based approaches employ geometric priors to extend the Expectation Maximization (EM) algorithm to augment statistical classification. In relatively homogeneous cases such as low grade gliomas, the outlier detection framework proposed by Prastawa et al. was shown to perform well.

Pixel-based approaches such as Fuzzy C-Means (FCM) using neighborhood labels, Conditional Random Fields, Bayesian model-aware affinities extending the SWA algorithm, and the more recent graph-based techniques combined with the Cellular-Automata (CA) algorithm have also achieved some success in tumor segmentation. However, processing issues with respect to contour initialization, noise reduction, intensity standardization, cluster selection, spatial registration, and the need for accurate manual seed-selection leaves substantial room for improvement. In addition, building a robust automated approach that does not require user intervention is very important, particularly for processing large datasets.

Sparsity in Tumor Segmentation

Sparse models form an important component in image understanding since they emulate the activity of neural receptors in the primary visual cortex of the human brain. Olshausen and Field demonstrated that learning sparse linear codes for natural images results in a family of localized, oriented, and bandpass features, similar to those found in the primary visual cortex. Sparsity of the coefficients has been exploited in a variety of signal, and image processing applications including compression, denoising, compressed sensing, source separation, face classification, and object recognition.

Despite its great applicability, the use of sparse models in complex visual recognition applications presents three main challenges: (i) linear generative model of sparse coding can be insufficient for modeling the non-linear relationship between the complex image features, (ii) in several visual recognition tasks, no single descriptor can efficiently model the whole data set, i.e., there is a need to integrate multiple image features into the sparse coding paradigm, and (iii) sparse models require data samples to be represented in the form of feature vectors, and it is not straightforward to extend them to the case of other forms such as pixel values, matrices or higher order tensors. In order to circumvent the aforementioned challenges, kernel learning methods can be incorporated in sparse coding. The kernel methods map the data samples into a high-dimensional feature space, using a non-linear transformation, in which the relationship between the features can be represented using linear models. By ensuring that the resulting feature space is a Hilbert space, kernel methods can work by considering only the similarity between the features, and not the features themselves. By developing approaches for sparse coding and dictionary learning in the feature space, frameworks can be designed for computer vision tasks such as recognition and segmentation.

In this disclosure, we develop a approach to automatically segment enhancing/active and necrotic tumor components from T1-weighted contrast-enhanced MR images. We propose to compute kernel sparse codes for the pixels in the image and perform pixel-based segmentation using those codes. Furthermore, we develop the kernel dictionary learning algorithm (e.g., kernel K-lines clustering) to learn kernel dictionaries for coding the pixels. The proposed algorithm for localizing the active tumor regions uses an ensemble kernel constructed using pixel intensities and their spatial locations. Each pixel is classified as belonging to a tumor or a non-tumor region using a linear support vector machine (SVM) on the kernel sparse codes. Finally, we propose a semi-automated segmentation technique for improved computational efficiency, wherein the user can initialize the tumor region. This approach eliminates the need to incorporate the spatial location information and reduces the number of pixels to be processed. In addition, we show that the complex linear SVM classifier can be replaced by a simple error-based classifier without compromising the segmentation quality. We evaluate the proposed algorithm on a set of T1-weighted contrast-enhanced MR images and compare the results with manual segmentation performed by an expert radiologist.

Sparse Coding and Dictionary Learning

Sparse models have become a significant paradigm in image understanding, since many naturally occurring images can be efficiently modeled as a sparse linear combination of elementary features. The set of elementary features, atoms, normalized to unit $l_2$ norm comprises the dictionary matrix. Given a sample $y \in \mathcal{R}^M$, and a dictionary $D \in \mathcal{R}^{M \times K}$, the generative model for sparse coding is $y=Dx+n$, where $x \in \mathcal{R}^K$ is the sparse code with a small number of non-zero coefficients and $n$ is the noise component. The sparse code can be computed by solving the convex problem $$\min_{x} \|y - Dx\|_2^2 + \beta\|x\|_1, \quad (1)$$

where $\|\cdot\|_1$ indicates the $l_1$ norm, and is a convex surrogate for the $l_0$ norm which counts the number of non-zero elements in a vector. Some of the algorithms used to solve (1) include the Basis Pursuit, feature-sign search and the least angle regression algorithm with the LASSO modification (LARS-LASSO). When presented with a sufficiently large set of training data samples, $Y=[y_i]^T_{i=1}$, the dictionary can be learned, and the corresponding sparse codes can be obtained by solving $$\min_{D,X} \|Y - DX\|_F^2 + \beta \sum_{i=1}^{T} \|x_i\|_1, \quad (2)$$

where $X=[x_i]^T_{i=1}$, and $\|\cdot\|_F$ denotes the Frobenius norm of the matrix. Equation (2) can be solved as an alternating minimization problem, where the dictionary is learned fixing the sparse codes, and the sparse codes are obtained fixing the dictionary. Dictionaries adapted to the data have been shown to provide superior performance when compared to pre-defined dictionaries in several applications. In addition to being useful in data representation problems, there has been a recent surge of interest in using sparse models in several supervised, semi-supervised and unsupervised learning tasks such as clustering and classification.

Kernel Sparse Coding for Tumor Segmentation

Sparse coding algorithms are typically employed for vectorized patches or feature vectors extracted from the images, using an over-complete dictionary. However, the proposed tumor identification algorithm aims to obtain sparse codes for the pixel values directly. This is trivial if we use the approach specified in (1), since $M=1$ in this case. Furthermore, in order to discriminate between the pixels belonging to multiple segments, we may need to consider the non-linear similarity between them. Though the linear generative model of sparse coding has been effective in several image understanding problems, it does not consider the non-linear similarities between the training samples.

It is typical in machine learning methods to employ the Kernel Trick to learn linear models in a feature space that captures the non-linear similarities. The Kernel Trick maps the non-linear separable features into a feature space $\mathcal{F}$ using a transformation $\Phi(.)$, in which similar features are grouped together. By performing sparse coding in the feature space $\mathcal{F}$, we can obtain highly discriminative codes for samples from different classes. Note that the choice of the non-linear transformation is crucial to ensure discrimination. The transformation $\Phi(.)$ is chosen such that $\mathcal{F}$ is a Hilbert space with the reproducing kernel $K(.,.)$ and hence the non-linear similarity between two samples in $\mathcal{F}$ can be measured as $K(y_i, y_j)=\Phi(y_i)^T \Phi(y_j)$. Note that the feature space is usually high-dimensional (sometimes infinite) and the closed form expression for the transformation $\Phi(.)$ may be intractable or unknown. Therefore, we simplify the computations by expressing them in terms of inner products $\Phi(y_i)^T \Phi(y_j)$, which can then be replaced using $K(y_i, y_j)$, the value of which is always known. This is referred to as the Kernel Trick. Note that in order for a kernel to be valid, the kernel function or the kernel matrix should be symmetric positive semidefinite according to Mercer's theorem.

In this disclosure, we use the Radial Basis Function (RBF) kernel of the form $K(y_i, y_j)=\exp(-\gamma(y_i-y_j)^2)$, which leads to discriminative sparse codes. As a simple demonstration, the difference between linear similarity of grayscale pixel intensities (0 to 255) and the non-linear similarities obtained using the RBF kernel ($\gamma=0.3$) is illustrated in FIG. 1. Specifically, FIG. 1 shows linear similarity ($y_i y_j$) (left), and shows non-linear similarity ($K(y_i, y_j)$) using an RBF kernel (right). The linear similarities depend predominantly on the individual intensities of the pixels and not on the closeness of intensities. Whereas, when the RBF kernel is used, the pixel intensities that are close to each other have high non-linear similarity irrespective of the intensities. Pixels with intensities that are far apart have zero non-linear similarity. Therefore, the pixelwise sparse codes that we obtain using such a kernel will behave similarly.

Kernel Sparse Coding

Given the feature mapping function $\Phi: \Re^M \to R^G$, the generative model in $\mathcal{F}$ for kernel sparse coding is given by $\Phi(y)=\Phi(D)x+n$. We denote the data sample y in the feature space as $\Phi(y)$ and the dictionary by $\Phi(D)=[\Phi(d_1), (d_2), \ldots, \Phi(d_K)]$. The kernel similarities $K(y_i, y_j)=\Phi(y_i)^T\Phi(y_j)$, $K(d_k, y)=\Phi(d_k)^T\Phi(y)$ and $K(d_k, d_l)=\Phi(d_k)^T\Phi(d_l)$ can be computed using pre-defined kernel functions (RBF in our case). All further computations in the feature space should be performed exclusively using kernel similarities. The problem of sparse coding in (1) can be posed in the feature space as $$\min_x \|\Phi(y) - \Phi(D)x\|_2^2 + \lambda\|x\|_1. \quad (3)$$

Expanding the objective in (3) we obtain $$\Phi(y)^T\Phi(y) - 2x^T\Phi(D)^T\Phi(y) + x^T\Phi(D)^T\Phi(D)x + \lambda\|x\|_1,$$

$$= K_{yy} - 2x^T K_{Dy} + x^T K_{DD} x + \lambda\|x\|_1, \quad (4)$$

$$= F(x) + \lambda\|x\|_1. \quad (5)$$

Here, $K_{yy}$ is the element $K(y, y)$, $K_{Dy}$ is a K×1 vector containing the elements $K(d_k, y)$, $\forall k=\{1, \ldots, K\}$ and $K_{DD}$ is a K×K matrix containing the kernel similarities between the dictionary atoms. Clearly, the modified objective function is similar to the sparse coding problem, except for the use of the kernel similarities. Hence, the kernel sparse coding problem can be efficiently solved using the feature-sign search algorithm or LARS. However, it is important to note that the computation of kernel matrices incurs additional complexity. Since the dictionary is fixed in (5), $K_{DD}$ is computed only once and the complexity of computing $K_{Dy}$ grows as O(MK).

Kernel Dictionary Design

Optimization of dictionaries in the feature space can be carried out by reposing the dictionary learning procedures using only the kernel similarities. Such non-linear dictionaries can be effective in yielding compact representations, when compared to approaches such as the kernel PCA, and in modeling the non-linearity present in the training samples. In this section, we will describe the formulation of a kernel dictionary learning procedure, and demonstrate its effectiveness in representation and discrimination.

The joint problem of dictionary learning and sparse coding in (2) is a generalization of 1-D subspace clustering. In order to design the dictionary $\Phi(D)$, we will adapt (2) to the feature space, with the constraint that only one element in the sparse code can be non-zero. This is a special case of the kernel dictionary learning proposed in H. V. Nguyen et al., Kernel Dictionary Learning, *Proceedings of the IEEE ICASSP* (2012). This procedure is equivalent to the kernel version of K-lines clustering, which attempts to fit K 1-D subspaces to the training data in $\mathcal{F}$. Though sophisticated kernel dictionaries can be designed, employing dictionaries obtained using this clustering procedure results in good performance for our tumor segmentation problem. The clustering procedure can be solved using $$\min_{A,X} \|\Phi(Y) - \Phi(Y)AX\|_F^2 \text{ such that } \|x_i\|_0 \leq 1, \forall i. \quad (6)$$

Each dictionary atom $\Phi(d_i)$ corresponds to a cluster center and each coefficient vector $x_i$ encodes the cluster association as well as the weight corresponding to the $i^{th}$ pixel. Let us define K membership sets $\{C_\kappa\}_{\kappa=1}^K$; where $C_k$ contains the indices of all training vectors that belong to the cluster k. The alternating optimization for solving (6) consists of two steps: (a) cluster assignment, which involves finding the association and weight of each training vector and hence updating the sets $\{C_\theta\}_{\kappa=1}^K$ and (b) cluster update, which involves updating the cluster center by finding the centroid of training vectors corresponding to each set $C_k$.

In the cluster assignment step, we compute the correlations of a training sample, with the dictionary atoms as $\Phi(y_i)^T\Phi(D)=K_{y_iY}A$. If the $k^{th}$ dictionary atom results in maximum absolute correlation, the index i is placed in set $C_k$, and the corresponding non-zero coefficient is the correlation value itself. For the cluster k, let $\Phi(Y_k)=\Phi(Y)E_k$ be the set of member vectors and $x_\kappa^R$ be the row of corresponding non-zero weights. The cluster update involves solving $$\min_{a_k} \|\Phi(Y)a_k x_k^R - \Phi(Y)E_k\|_F^2. \quad (7)$$

Denoting the singular value decomposition of $$\Phi(Y_k)=U_k\Sigma_k V_k^T, \quad (8)$$

the rank-1 approximation, which also results in the optimal solution for (7), is given by $$\Phi(Y)a_k x_k^R = u_{k1}\sigma_{k1} v_{k1}^T, \quad (9)$$

where $\sigma_{k1}$ is the largest singular value, and $u_{k1}$ and $v_{k1}$ are the columns of $U_k$ and $V_k$ corresponding to that singular value. Equation (9) implies that $\Phi(Y)a_k = u_{k1}$ and $x_\kappa^R = \sigma_{k1} v_{k1}^T$. Let the eigen decomposition of $K_{\kappa\kappa}^{Y^T}$ be $V_k \Delta_k V_k^T$ and hence we have $\sigma_{k1}=\sqrt{\Delta_\kappa(1,1)}$, assuming the eigen values are in descending order. From (8), we also have $\Phi(Y_k)v_{k1}=\sigma_{k1}u_{k1}$. Substituting for $\Phi(Y_k)$ and $u_{k1}$, we obtain $\Phi(Y)E_k v_{k1}=\sigma_{k1}\Phi(Y)a_k$, which results in $$a_k = \sigma_{k1}^{-1} E_k v_{k1}. \quad (10)$$

Note that $a_k$ completely defines $d_k$. The cluster assignment and update steps are repeated until convergence, i.e., when $\{C_\kappa\}_{\kappa=1}^K$ does not change over iterations.

Representation

Figure 2:
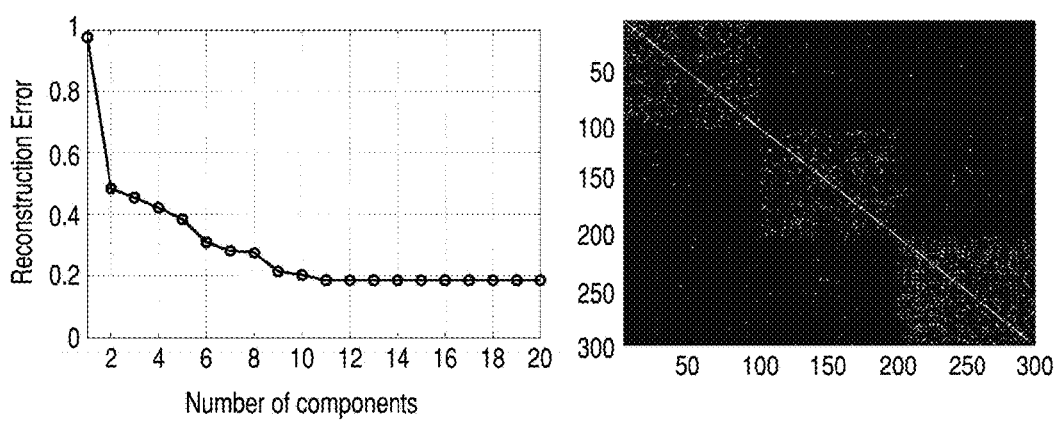
FIG. 2 shows the reconstruction error obtained for a test sample using kernel sparse coding, for different values of sparsity (left), and the similarity between kernel sparse codes of samples drawn from the 3 different classes in the USPS dataset (right)

Kernel sparse coding can be used as an alternative to approaches such as kernel PCA for efficient data representation. Though complete reconstruction of the underlying data from the kernel sparse codes requires computation of pre-images, test samples can be well approximated using the learned kernel dictionaries. As a demonstration, we consider the class of digit 2 from the USPS dataset and use a subset of images for training a kernel dictionary using kernel dictionary learning algorithms (e.g., kernel K-lines clustering). We then compute sparse code for a test sample z, different from the training set, and compute the reconstruction error as $\|\Phi(z)-\Phi(D)a\|_2^2$. FIG. 2 (left) shows the reconstruction error obtained for a test sample using kernel sparse coding, for different values of sparsity, $\{1, \ldots, 20\}$.

Discrimination

In addition to efficiently modeling data samples, kernel sparse coding is well suited for supervised learning tasks. Since the non-linear similarities between the training samples are considered while learning the dictionary, the resulting codes are highly discriminative. As a demonstration, we consider 100 training samples each from 3 different classes in the USPS dataset (Digits 3, 4 and 7). We obtain the kernel sparse codes for all the samples and compute the normalized cross correlation between the sparse features. In cases of high discrimination, we expect the features belonging to a class to be highly similar to each other compared to samples from other classes. The block-wise structure in the normalized correlation plot in FIG. 2 (right), which shows the similarity between the kernel sparse codes of samples drawn from the 3 different classes in the USPS dataset, evidences the discrimination power of the kernel sparse codes. Since the kernel codes of the samples belonging to the same class are highly similar, FIG. 2 (right) shows a block-wise structure in the normalized correlation plot.

Proposed Automated Tumor Segmentation Algorithm

The proposed algorithm employs a pixel-based approach to determine tumor regions in the MR image. In order to determine if a pixel belongs to a tumor region, adaptive thresholding techniques can be used. However, building more sophisticated tools can improve segmentation performance. In this section, we describe the proposed algorithm for automated tumor segmentation based on kernel sparse codes.

To perform tumor segmentation, we need to identify pixels that can possibly constitute a tumor region based on intensity. Though segmentation is as an unsupervised learning problem, we can pose it as a supervised learning problem since we can easily obtain at least a few training images with tumor regions marked by an expert. Hence, we propose to obtain kernel dictionaries using the training samples and learn a 2-class classifier (Tumor vs Non-tumor). Furthermore, in order to localize the tumor regions in the image, we need to incorporate additional constraints to ensure connectedness among pixels in a segment. This can be addressed by building a spatial location kernel and fusing it with the intensity kernel.

Combining Multiple Features

The use of multiple features to more precisely characterize images has been a very successful approach for several classification tasks. Though this method provides the flexibility of choosing features to describe different aspects of the underlying data, the resulting representations are high-dimensional and the descriptors can be very diverse. Hence, there is a need to transform the features to a unified space that facilitates the recognition tasks, and construct low dimensional compact representations for the images in the unified space.

Let us assume that a set of R diverse descriptors are extracted from a given image. Since the kernel similarities can be used to fuse the multiple descriptors, we need to build the base kernel matrix for each descriptor. Given a suitable distance function $d_r$, which measures the distance between two samples for the feature r, we can construct the kernel matrix as $$K_r(i,j)=K_r(y_i,y_j)=\exp(-\gamma d_r^2(y_i,y_j)), \quad (11)$$

where $\gamma$ is a positive constant. Given the R base kernel matrices, $\{K_r\}_{r=1}^R$, we can construct the ensemble kernel matrix as $$K = \sum_{r=1}^R \beta_r K_r, \forall \beta_r \geq 0. \quad (12)$$

Note that the ensemble matrix can be constructed in other ways also. Alternatively, the descriptors can be fused as $$K=K_1 \odot K_2 \odot \ldots \odot K_R, \quad (13)$$

where $\odot$ denotes the Hadamard product between two matrices. Performing sparse coding using the ensemble kernel matrices will take the R features into account. Note that when combining kernel matrices we need to ensure that the resulting kernel matrix also satisfies the Mercer's conditions.

Algorithm

Figure 3:
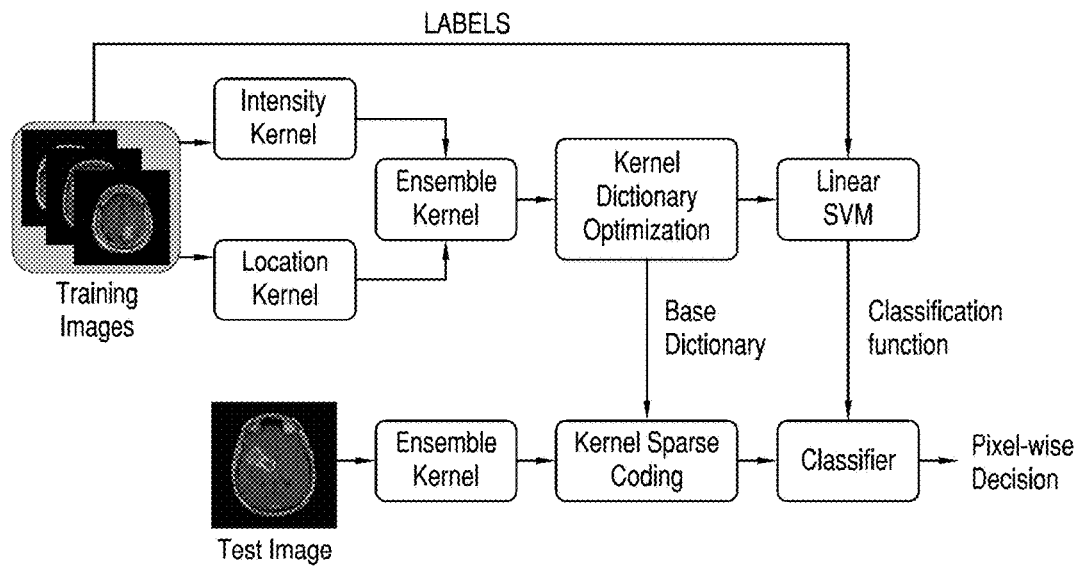
FIG. 3 illustrates a proposed algorithm for automated tumor segmentation, according to an embodiment.

A proposed algorithm for automated tumor segmentation is illustrated in FIG. 3. For a set of training samples, the ensemble kernel dictionary can be obtained using Kernel K-lines clustering procedure, and a 2-class linear classifier (e.g., SVM) can be used to classify the pixels. In the rest of this disclosure, we refer to this as the Kernel Sparse Coding-based Automated (KSCA) segmentation algorithm. In the training stage, it is assumed that the location of the tumor pixels are known in the ground truth training images. For a subset of T pixels (both positive and negative examples) obtained from the training images, we compute the intensity kernel matrix, $K_I \in \mathfrak{R}^{T \times T}$, by employing an RBF kernel on the pixel intensity values. In addition, the spatial location kernel matrix $K_L$ is constructed as $$K_L(i, j) = K_L(y_i, y_j) = \begin{cases} \exp^{\|L_i-L_j\|_2^2}, & \text{if } j \in \mathcal{N}(i), \\ 0, & \text{otherwise.} \end{cases} \quad (14)$$

Here, $\mathcal{N}(i)$ denotes the neighborhood of the pixel $y_i$, and $L_i$ and $L_j$ are the locations of the pixels, $y_i$ and $y_j$ respectively. We fuse the intensity and spatial location kernel matrices to obtain the ensemble kernel matrix, $K=K_I \odot K_L$.

The sparse codes obtained with a dictionary learned in the ensemble feature space model the similarities with respect to both intensity and location of pixels. A set of training images, with active tumor regions, are used to learn a kernel dictionary with the kernel K-lines clustering procedure. Using the kernel sparse codes belonging to tumor and non-tumor regions, we learn 2-class linear SVM to classify the pixel. For a test image, we obtain the required ensemble kernel matrices and compute the kernel sparse codes using the learned dictionary. Finally, the SVM classifier can be used to identify the pixels belonging to an active tumor region. The impact of combining diverse features using kernel sparse coding is evidenced by the accurate segmentation results.

Complexity Reduction Using a Semi-Automated Approach

Figure 4:
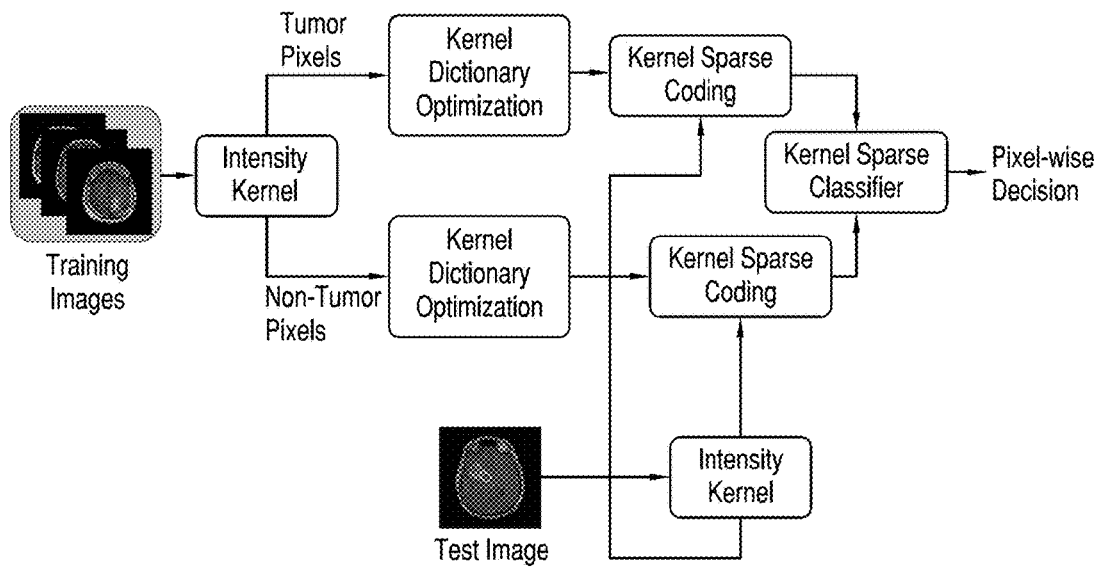
FIG. 4 illustrates a proposed approach for complexity reduction in the proposed algorithm of the embodiment of FIG. 3.

A proposed approach for complexity reduction in the proposed algorithm is illustrates in FIG. 4. By allowing the use to initialize the tumor region in a test image, the need for incorporating locality information can be eliminated. Furthermore, the SVM classifier can be replaced by a simple reconstruction error-based classifier.

The amount of training required and the computational complexity are two important factors that can determine the efficiency of an automated segmentation algorithm. Since the dictionary training is performed using pixels, the number of training images used is quite limited. Though the computational complexity of the automated segmentation algorithm described earlier is comparable to several existing methods, its efficiency can be further improved by allowing the user to initialize the tumor region. Computing the kernel sparse codes for all pixels in a test image incurs the maximum complexity and hence initializing the tumor regions drastically reduces the number of pixels to be processed. Furthermore, there is no need to explicitly include the location information in the algorithm, since the tumor region has already been localized by the user. Hence, the classification can be carried out by using a simple error-based classifier on the kernel sparse codes. We refer to this as the Kernel Sparse Coding-based Semi-Automated (KSCSA) segmentation approach. We observed from our experiments that for an average sized tumor region, we achieve significant speedup by using the semi-automated approach. However, the segmentations obtained using the two methods are quite comparable, though the automated approach can potentially generate more false positives when compared to the semi-automated approach.

Given a set of training images containing active tumor regions, we use the tumor and non-tumor pixels to train two separate kernel dictionaries. We construct two RBF kernel matrices on the pixel intensities and employ the kernel K-lines clustering algorithm to learn the tumor and non-tumor dictionaries, $\Phi(D_T)$ and $\Phi(D_N)$, respectively. Note that dictionary learning is performed only once, and as we will show in our experimental results, the dictionaries generalize well to reasonably large datasets.

For a test image, we obtain kernel sparse codes for each pixel $y_i$ using $\Phi(D_T)$ and $\Phi(D_N)$, and denote the respective sparse codes as $x_i^T$ and $x_i^N$. Since the dictionaries are optimized for two different classes of pixel intensities, we expect the tumor pixels to be better modeled by the tumor dictionary. Hence we classify a pixel as belonging to an active tumor region if the approximation error obtained with the tumor dictionary is less than that obtained with the non-tumor dictionary:

$$\mathcal{J}(y_i) = \begin{cases} \text{Tumor,} & \text{if } E_N - E_T \geq \epsilon, \\ \text{Non-tumor,} & \text{otherwise.} \end{cases} \quad (15)$$

Here the approximation errors with respect to the two dictionaries are $E_N = \|\Phi(y_i) - \Phi(D_N)x_i^N\|_2$ and $E_T = \|\Phi(y_i) - \Phi(D_T)x_i^T\|_2$, respectively. Note that the threshold for the error difference, $\epsilon$, can be tuned using a validation dataset before applying the algorithm to the test data.

Experiments

In this section, we provide details about the datasets used to evaluate our algorithm and present the segmentation results. The results are compared to manual segmentations performed by a radio-oncology specialist, based on both the subjective visual quality and quantitative standards such as Accuracy (Acc) and Correspondence Ratio (CR).

Dataset

The algorithm was tested on a set of T1-weighted (spin echo) contrast-enhanced, 2-D Dicom format images acquired with a 1.5 T GE Genesis Signa MR scanner. Each axial slice was 5 mm thick with a 7.5 mm gap between slices, and the size of the image matrix was 256×256. Patients were administered a 20 cc Bolus of Gadolinum contrast agent, and were already diagnosed with Glioblastoma Multiforme (GBM), the most common and dangerous malignant primary brain tumor. These tumors are characterized by jagged boundaries with a ring enhancement, possibly a dark core necrotic component, and are accompanied by edema (swelling). The ground truth (GT) images were obtained from the manual segmentation carried out by an expert radiologist at the St. Joseph's Hospital and Medical Center in Phoenix. We tested our algorithm on the pre- and post-treatment images for 9 patients where all the slices (approximately 175) showed the presence of GBM.

Benchmark Algorithm—Active Contour Method

We compare the segmentation results of our proposed algorithms to the widely used Chan-Vese Active Contour Method (ACM). The main goal of this region based method is to minimize the energy function defined by the means of the pixel intensities inside and outside the initial level set curve. Note that this algorithm is not completely automated. The initial level set formulation is conveyed to the algorithm by enabling the user to draw a binary mask over the region of interest in the image. The binary mask is converted to a Signed Distance Function (SDF), such that the region within the curve is assigned positive values, increasing with distance, and the region outside the curve is given increasing negative values, with the distance from the curve. The SDF enables interaction with the energy function as it associates the modification and movement of the initial level set formulation with the change in energy statistics in the two regions. An update occurs with every iteration, wherein the curve evolves and a new SDF is generated based on the previous iteration. The algorithm stops updating the initial level set formulation when the energy is minimized, and further evolution of the curve leads to an increase in the energy value achieved in the previous iteration.

Since this algorithm is not based on gradient methods, and deals with balancing the energy on both sides of the curve, it achieves good results even when the image is blurred. One of the main advantages of this algorithm is that it relies on global properties rather than just taking into account local properties, such as gradients. Furthermore, it provides improved robustness in the presence of noise.

Results

Simulations were carried out independently for both the semi-automated and automated algorithms for every axial slice. For both of the proposed algorithms, the parameter $\gamma$ for the RBF kernel was set to 0.3, and the dictionary size was fixed at 256. In the automated approach, we computed the ensemble kernel for 15,000 randomly chosen pixels from the training set. In the reduced complexity semi-automated case, the tumor and non-tumor dictionaries were learned using 10,000 randomly chosen pixels from tumor and non-tumor regions respectively. The parameter $\beta = 0.1$ was used for sparse coding using the feature sign search algorithm.

The resulting segmented images were compared to the ground truth and performance was measured using the metrics Accuracy (Acc) and Correspondence Ratio (CR) computed as $$Acc = \frac{TP}{\text{Total \# tumor pixels in the } GT \text{ image}}, \quad (16)$$

and $$CR = \frac{TP - 0.5 FP}{\text{Total \# tumor pixels in the } GT \text{ image}}, \quad (17)$$

where TP indicates the number of true positives (the pixels indicated as tumorous by the ground truth and our algorithm), and FP denotes the number of false positives (pixels indicated as non-tumorous by the ground truth, but tumorous by our algorithm). The other unknown parameter in the KSCSA approach is the error threshold $\epsilon$, used for classifying the pixels. Table 1 below shows a comparison of the tumor segmentation performance obtained using (a) Active contour method (ACM), (b) Kernel sparse coding-based automated segmentation algorithm (KSCA), and (c) Kernel sparse coding-based semi-automated segmentation algorithm (KSCSA). For each patient, results for a few sample images (pre- and post-treatment) are shown. In each case, the accuracy and correspondence ratio of the segmentation in comparison to expert-marked ground truth are presented.

TABLE 1

| Image Set | ACM Acc | ACM CR | KSCA Acc | KSCA CR | KSCSA Acc | KSCSA CR |
|---|---|---|---|---|---|---|
| Patient 1: | | | | | | |
| Pre | 0.81 | 0.71 | 0.87 | 0.86 | 0.92 | 0.91 |
| Pre | 0.42 | 0.12 | 0.66 | 0.33 | 0.69 | 0.41 |
| Pre | 0.48 | 0.22 | 0.78 | 0.57 | 0.78 | 0.62 |
| Pre | 0.43 | 0.15 | 0.72 | 0.6 | 0.71 | 0.64 |
| Pre | 0.42 | 0.13 | 0.67 | 0.48 | 0.68 | 0.47 |
| Patient 2: | | | | | | |
| Pre | 0.22 | 0.16 | 0.46 | 0.4 | 0.49 | 0.43 |
| Pre | 0.95 | 0.93 | 0.96 | 0.92 | 0.97 | 0.93 |
| Pre | 1.00 | 0.99 | 1.00 | 0.98 | 0.99 | 0.99 |
| Pre | 0.87 | 0.8 | 0.95 | 0.81 | 0.97 | 0.82 |
| Pre | 0.95 | 0.93 | 0.97 | 0.94 | 0.98 | 0.91 |
| Patient 3: | | | | | | |
| Pre | 0.97 | 0.96 | 0.97 | 0.96 | 0.98 | 0.96 |
| Pre | 0.91 | 0.86 | 0.95 | 0.9 | 0.98 | 0.96 |
| Post | 1.00 | 1.00 | 0.99 | 0.97 | 1.00 | 0.99 |
| Post | 0.76 | 0.64 | 0.98 | 0.81 | 0.97 | 0.85 |
| Post | 0.81 | 0.71 | 0.83 | 0.73 | 0.86 | 0.72 |
| Patient 4: | | | | | | |
| Pre | 0.50 | 0.25 | 0.64 | 0.57 | 0.70 | 0.65 |
| Pre | 0.53 | 0.29 | 0.98 | 0.84 | 0.97 | 0.88 |
| Pre | 0.93 | 0.90 | 0.91 | 0.88 | 0.92 | 0.90 |
| Pre | 0.40 | 0.10 | 0.91 | 0.82 | 0.94 | 0.90 |
| Post | 0.73 | 0.6 | 0.79 | 0.67 | 0.82 | 0.72 |
| Patient 5: | | | | | | |
| Pre | 0.94 | 0.90 | 0.96 | 0.88 | 0.97 | 0.89 |
| Pre | 0.81 | 0.71 | 0.91 | 0.84 | 0.90 | 0.83 |
| Pre | 0.54 | 0.31 | 0.68 | 0.59 | 0.70 | 0.66 |
| Pre | 0.92 | 0.88 | 0.98 | 0.96 | 0.98 | 0.97 |
| Pre | 0.78 | 0.66 | 0.98 | 0.9 | 0.95 | 0.91 |
| Patient 6: | | | | | | |
| Pre | 0.98 | 0.97 | 1.00 | 0.96 | 0.99 | 0.99 |
| Pre | 0.62 | 0.43 | 0.96 | 0.94 | 0.95 | 0.94 |
| Pre | 0.87 | 0.81 | 0.92 | 0.91 | 0.97 | 0.96 |
| Post | 0.91 | 0.87 | 0.92 | 0.87 | 0.93 | 0.91 |
| Post | 0.93 | 0.89 | 0.95 | 0.88 | 0.95 | 0.91 |
| Patient 7: | | | | | | |
| Pre | 0.44 | 0.16 | 0.70 | 0.62 | 0.71 | 0.66 |
| Pre | 0.61 | 0.41 | 0.90 | 0.73 | 0.90 | 0.82 |
| Pre | 0.82 | 0.73 | 0.91 | 0.86 | 0.90 | 0.88 |
| Pre | 0.83 | 0.74 | 0.90 | 0.81 | 0.90 | 0.79 |
| Pre | 0.94 | 0.91 | 0.94 | 0.92 | 0.95 | 0.91 |
| Patient 8: | | | | | | |
| Pre | 0.77 | 0.65 | 0.95 | 0.79 | 0.98 | 0.87 |
| Pre | 0.73 | 0.60 | 0.91 | 0.8 | 0.95 | 0.84 |
| Post | 0.53 | 0.29 | 0.92 | 0.79 | 0.87 | 0.82 |
| Post | 0.97 | 0.95 | 0.97 | 0.95 | 0.97 | 0.95 |
| Post | 0.99 | 0.99 | 0.99 | 0.99 | 0.99 | 0.99 |
| Patient 9: | | | | | | |
| Pre | 0.94 | 0.91 | 0.95 | 0.93 | 0.95 | 0.94 |
| Pre | 0.95 | 0.93 | 0.98 | 0.96 | 0.99 | 0.94 |
| Post | 0.47 | 0.21 | 0.87 | 0.75 | 0.88 | 0.78 |
| Post | 0.63 | 0.44 | 0.85 | 0.84 | 0.87 | 0.82 |
| Post | 0.82 | 0.72 | 0.91 | 0.88 | 0.94 | 0.86 |

Figure 5:
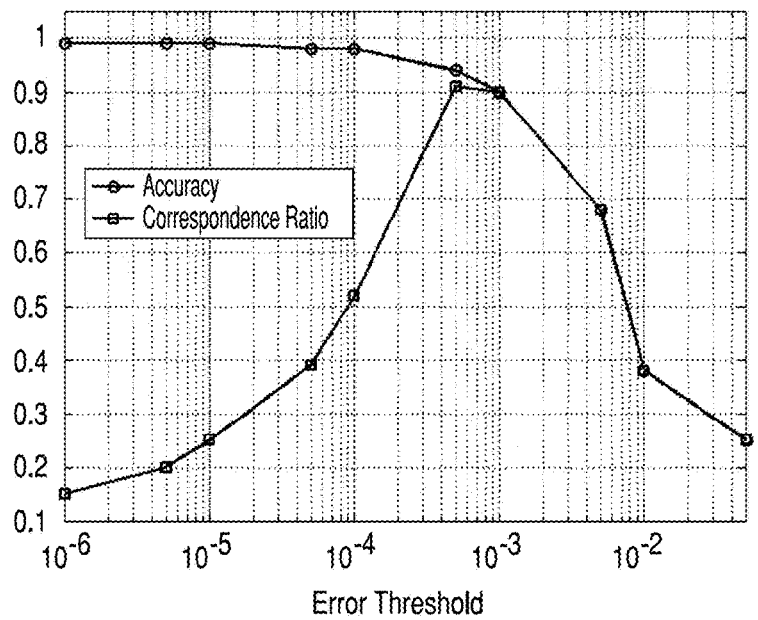
FIG. 5 illustrates the relationship between Acc and CR versus the error threshold ($\epsilon$) for two example images.
Figure 5:
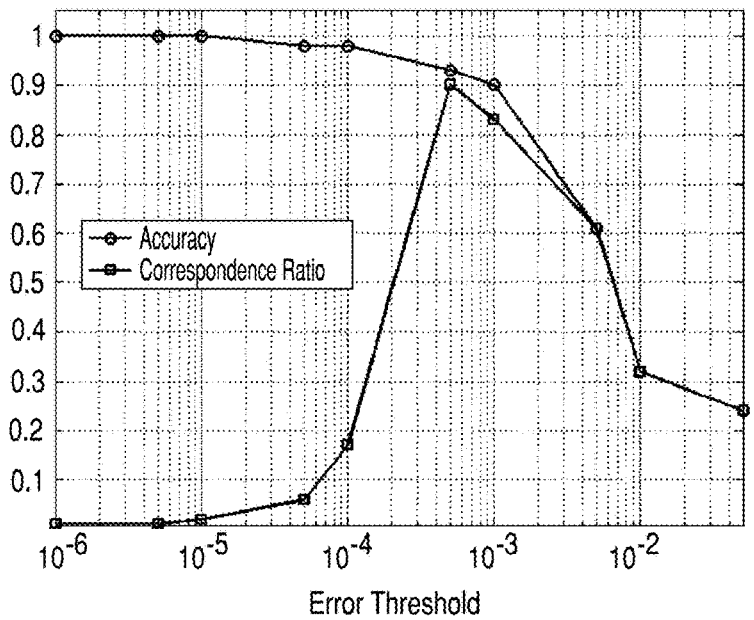

FIG. 5 shows the relationship between Acc and CR versus the error threshold ($\epsilon$) for two example images. The Acc and CR are plotted against different values of the error threshold $\epsilon$ for the two example images. An appropriate threshold that results in high Acc and CR, can be chosen using a validation dataset. The $\epsilon$ value was fixed at an appropriate value that resulted in high Acc and CR values on a validation dataset.

Figure 6:
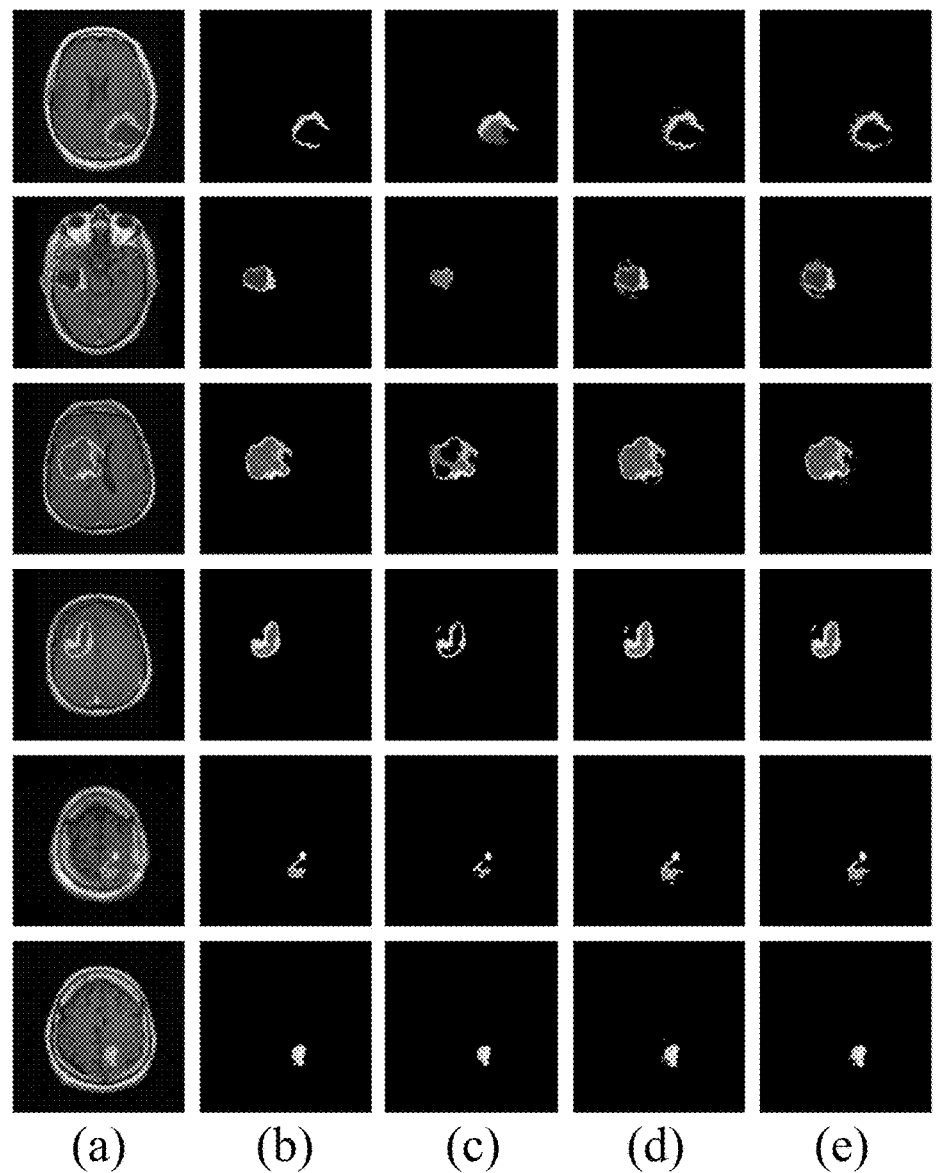
FIG. 6 illustrates the tumor segmentation results, with the original and segmented images for a few example cases, showing from left to right, (a) the original images; (b) Ground Truth (GT) marked by an expert radiologist; (c) Segmentation obtained using the active contour method; (d) Segmentation obtained using the KSCA algorithm; and (e) Segmentation obtained using the KSCSA algorithm.

FIG. 6 shows the tumor segmentation results, with the original and segmented images for a few example cases. From left to right on each row, FIG. 6 shows (a) the original images; (b) Ground Truth (GT) marked by an expert radiologist; (c) Segmentation obtained using the active contour method; (d) Segmentation obtained using the KSCA algorithm; and (e) Segmentation obtained using the KSCSA algorithm. In all cases, the proposed algorithms provide superior quality segmentation when compared to the benchmark algorithm.

In each case, the expert-marked ground truth is shown along with the results obtained using the ACM and the proposed algorithms. Both the proposed semi-automated and automated segmentation methods outperformed the benchmark method, and obtained high Acc and CR values as demonstrated by the extensive results in Table 1. We observed that the performance of the automated algorithm (KSCA) is equivalent to that of the semi-automated algorithm (KSCSA) in many cases and very closely comparable in the remaining cases. As expected, the semi-automated algorithm is significantly faster when compared to the automated approach. On an average, the proposed semi-automated algorithm takes about 8 seconds (measured using MATLAB R2010b on a 2.8 GHz, Intel i7 desktop) in comparison to 120 seconds taken by the automated algorithm. Note that, the average time reported for the semi-automated algorithm does not include the time taken by the user to initialize the tumor region.

An automated segmentation technique for detecting brain tumors was proposed in this disclosure. In the new approach, we constructed ensemble kernel matrices using the pixel intensities and their spatial locations, and obtained kernel dictionaries for sparse coding pixels in a non-linear feature space. The resulting sparse codes were used to train a linear SVM classifier that determines if a pixel in the image belongs to an active tumor region. Furthermore, a semi-automated segmentation approach was proposed that uses two kernel dictionaries to model the tumor and non-tumor pixels respectively and employs a simple error-based classifier. Using simulations on a real dataset obtained for 9 different patients, we demonstrated that both of the proposed approaches resulted in accurate tumor identifications in comparison to the widely used Chan-Vese active contour method. Certain embodiments extend the proposed approaches to include other types of MR imaging methods such as T2-weighted, FLAIR, perfusion-weighted, and diffusion-weighted images. Segmentation along with volumetric registration on different slices can be used to quantify the volume of the tumor region and model the growth of tumors over a period of time. The proposed algorithms can also be extended to identify tumors by computing kernel sparse codes for three dimensional (3-D) volumetric data instead of two dimensional (2-D) images.

Identifying tumor regions in MRI images using a robust and automated method is of significant value in clinical diagnosis and disease modeling. Particular embodiments focus on automatic identification and segmentation of glioblastoma multiforme (GBM), an aggressive and common brain tumor from T1-weighted MRI scans. Currently, several region-based and pixel-based methods are available for identifying tumor regions. However, they are challenged by factors such as initialization, sensitivity to noise and intensity variations, need for accurate spatial registration to other brain images, and manual selection of good "seed" samples or clusters. Furthermore, well-known region-based methods such as active contours are sensitive to initialization and have a high computational cost.

A number of embodiments overcome many of the issues in the previous methods by using feature space sparse methods that are robust to both size and shape of the tumor. By fusing both intensity and spatial location information of the pixels, this technique can perform automatic localization of tumor regions requiring no intervention or feedback from the user. In order to train the system, only a few expert-segmented training images are necessary in some embodiments. For a new test image, the system obtains sparse codes from every pixel and they are used to classify if that pixel belongs to the tumor region. When the user provides a rough initial estimate of the tumor in a test image, the proposed system can provide a highly accurate segmentation at near-real-time speed.

Certain aspects of particular embodiments include:
1. Computing pixel-wise sparse codes for each pixel in the MRI tumor images, in contrast to other sparse coding approaches that compute patch-wise or region-wise sparse codes. Both spatial location and the intensity information are fused to obtain the dictionary and the codes.
2. Utilizing expert-segmented training images, where the tumor regions are clearly marked, to learn a classifier, thereby re-posing the segmentation problem into a problem of classification, leading to an improved accuracy.
3. Automatically localizing the tumor regions for a test image, by testing the sparse code for each pixel with the classifier.
4. Achieving significant complexity reduction with highly accurate segmentation, when the user provides a rough initial estimate of the tumor region.

Existing methods for tumor segmentation are either region-based or pixel based. Region based methods such as active contours are sensitive to initialization and have a high computation cost. Pixel-based approaches such as fuzzy C-means and recent graph-based techniques such as the Cellular-Automata algorithm have also achieved some success in tumor segmentation. However, many existing methods are challenged by factors such as initialization, sensitivity to noise and intensity variations, need for accurate spatial registration to other brain images, manual selection of good "seed" samples or clusters. The proposed invention uses feature space sparse methods and hence it is robust to the change in size/shape of tumors. Since it uses locally extracted features, it also handles intensity variations across different regions effectively. Being a sparsity based method, it is naturally immune to various types of noise present in brain images. Expert-segmented images are used to provide the training examples, and hence the method is fully automated in identifying the tumor regions, requiring no user intervention. Significant complexity reduction can be achieved if a rough initial estimate of the tumor regions is provided. Various embodiments combine the advantages of traditional graph based methods in providing a good segmentation along with the power of feature space methods to discriminate well across tumor and non-tumor regions.

Figure 7:
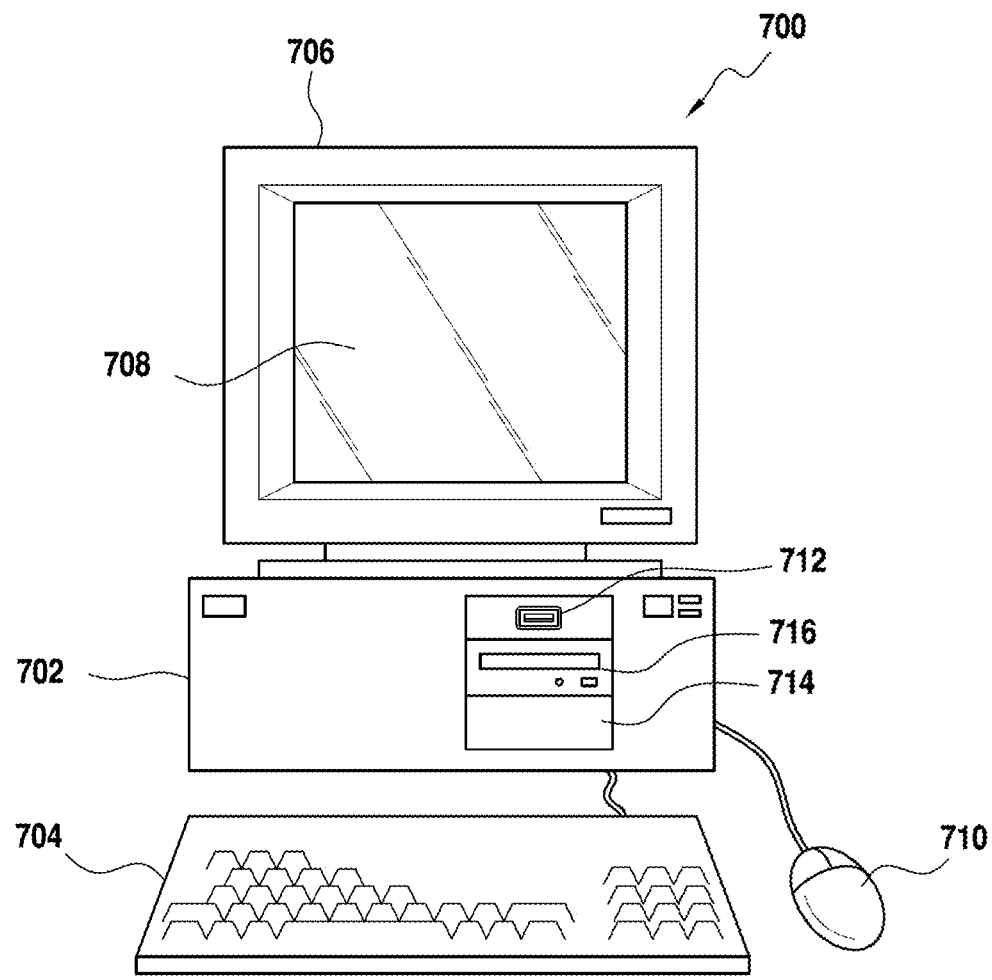
FIG. 7 illustrates a computer system that is suitable for implementing an embodiment of the computer system illustrated in FIG. 12, and for implementing one or more embodiments of the methods disclosed herein.
Figure 8:
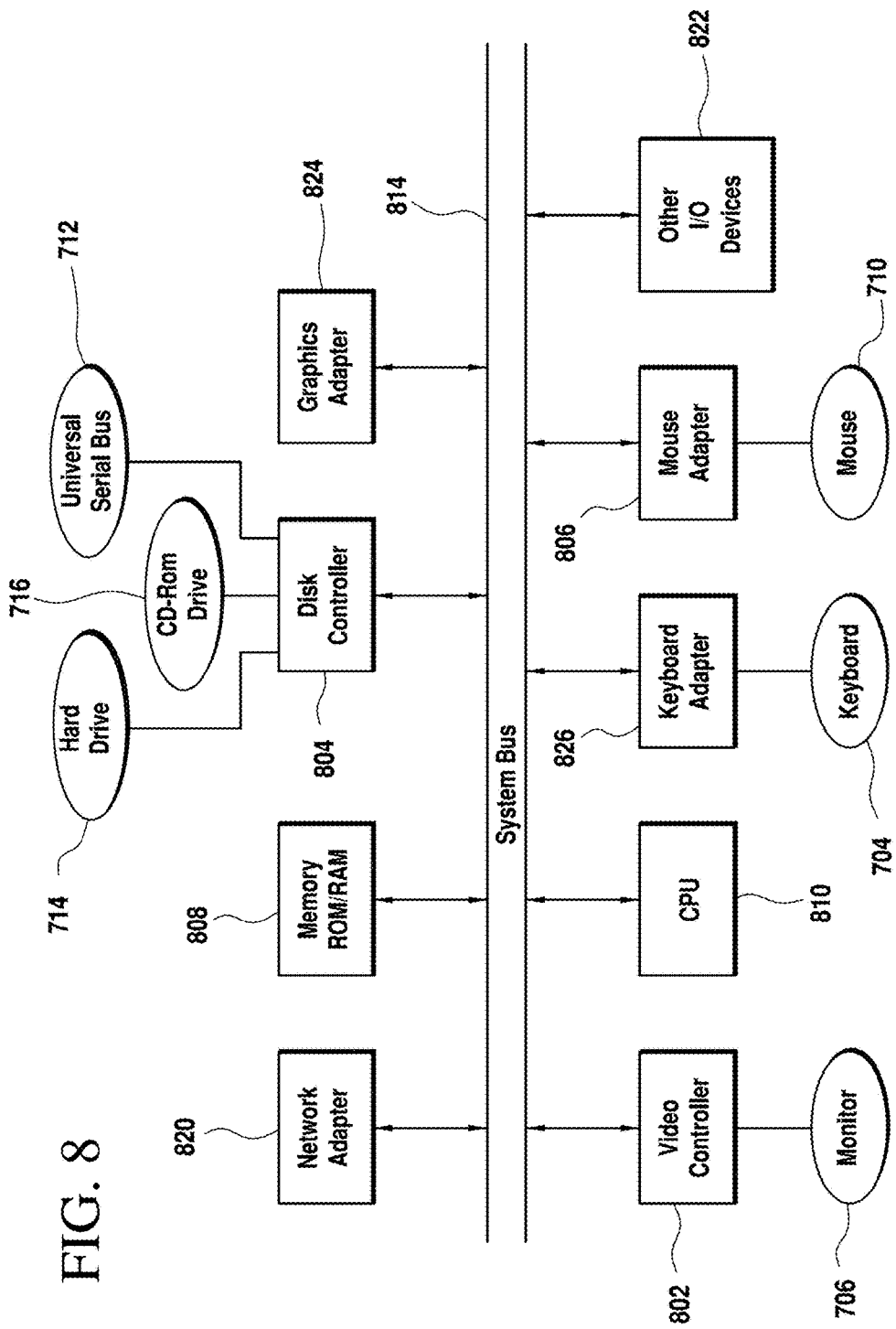
FIG. 8 illustrates a representative block diagram of an example of the elements included in the circuit boards inside a chassis of the computer system of FIG. 7.

FIG. 7 illustrates an exemplary embodiment of computer system 700, all of which or a portion of which can be suitable for implementing the techniques described above. As an example, a different or separate one of chassis 702 (and its internal components) can be suitable for implementing the techniques described above. Furthermore, one or more elements of computer system 700 (e.g., refreshing monitor 706, keyboard 704, and/or mouse 710, etc.) can also be appropriate for implementing the techniques described above. Computer system 700 comprises chassis 702 containing one or more circuit boards (not shown), Universal Serial Bus (USB) port 712, Compact Disc Read-Only Memory (CD-ROM) and/or Digital Video Disc (DVD) drive 716, and hard drive 714. A representative block diagram of the elements included on the circuit boards inside chassis 702 is shown in FIG. 8. Central processing unit (CPU) 810 in FIG. 8 is coupled to system bus 814 in FIG. 8. In various embodiments, the architecture of CPU 810 (FIG. 8) can be compliant with any of a variety of commercially distributed architecture families.

Continuing with FIG. 8, system bus 814 also is coupled to memory storage unit 808, where memory storage unit 808 comprises both read only memory (ROM) and random access memory (RAM). Non-volatile portions of memory storage unit 808 or the ROM can be encoded with a boot code sequence suitable for restoring computer system 700 (FIG. 7) to a functional state after a system reset. In addition, memory storage unit 808 can comprise microcode such as a Basic Input-Output System (BIOS). In some examples, the one or more memory storage units of the various embodiments disclosed herein can comprise memory storage unit 808, a USB-equipped electronic device, such as, an external memory storage unit (not shown) coupled to universal serial bus (USB) port 712 (FIGS. 7-8), hard drive 714 (FIGS. 7-8), and/or CD-ROM or DVD drive 716 (FIGS. 7-8). In the same or different examples, the one or more memory storage units of the various embodiments disclosed herein can comprise an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Some examples of common operating systems can comprise Microsoft® Windows® operating system (OS), Mac® OS, UNIX® OS, and Linux® OS.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 810.

In the depicted embodiment of FIG. 8, various I/O devices such as disk controller 804, graphics adapter 824, video controller 802, keyboard adapter 826, mouse adapter 806, network adapter 820, and other I/O devices 822 can be coupled to system bus 814. Keyboard adapter 826 and mouse adapter 806 are coupled to keyboard 704 (FIGS. 7-8) and mouse 710 (FIGS. 7-8), respectively, of computer system 700 (FIG. 7). While graphics adapter 824 and video controller 802 are indicated as distinct units in FIG. 8, video controller 802 can be integrated into graphics adapter 824, or vice versa in other embodiments. Video controller 802 is suitable for refreshing monitor 706 (FIGS. 7-8) to display images on a screen 708 (FIG. 7) of computer system 700 (FIG. 7). Disk controller 804 can control hard drive 714 (FIGS. 7-8), USB port 712 (FIGS. 7-8), and CD-ROM drive 716 (FIGS. 7-8). In other embodiments, distinct units can be used to control each of these devices separately.

In some embodiments, network adapter 820 can comprise and/or be implemented as a WNIC (wireless network interface controller) card (not shown) plugged or coupled to an expansion port (not shown) in computer system 700 (FIG. 7). In other embodiments, the WNIC card can be a wireless network card built into computer system 700 (FIG. 7). A wireless network adapter can be built into computer system 700 (FIG. 7) by having wireless communication capabilities integrated into the motherboard chipset (not shown), or implemented via one or more dedicated wireless communication chips (not shown), connected through a PCI (peripheral component interconnector) or a PCI express bus of computer system 700 (FIG. 7) or USB port 712 (FIG. 7). In other embodiments, network adapter 820 can comprise and/or be implemented as a wired network interface controller card (not shown).

Although many other components of computer system 700 (FIG. 7) are not shown, such components and their interconnection are well known to those of ordinary skill in the art. Accordingly, further details concerning the construction and composition of computer system 700 (FIG. 7) and the circuit boards inside chassis 702 (FIG. 7) are not discussed herein.

When computer system 700 in FIG. 7 is running, program instructions stored on a USB-equipped electronic device connected to USB port 712, on a CD-ROM or DVD in CD-ROM and/or DVD drive 716, on hard drive 714, or in memory storage unit 808 (FIG. 8) are executed by CPU 810 (FIG. 8). A portion of the program instructions, stored on these devices, can be suitable for carrying out at least part of the techniques described above.

Although computer system 700 is illustrated as a desktop computer in FIG. 7, there can be examples where computer system 700 may take a different form factor while still having functional elements similar to those described for computer system 700. In some embodiments, computer system 700 may comprise a single computer, a single server, or a cluster or collection of computers or servers, or a cloud of computers or servers. Typically, a cluster or collection of servers can be used when the demand on computer system 700 exceeds the reasonable capability of a single server or computer.

Figure 9:
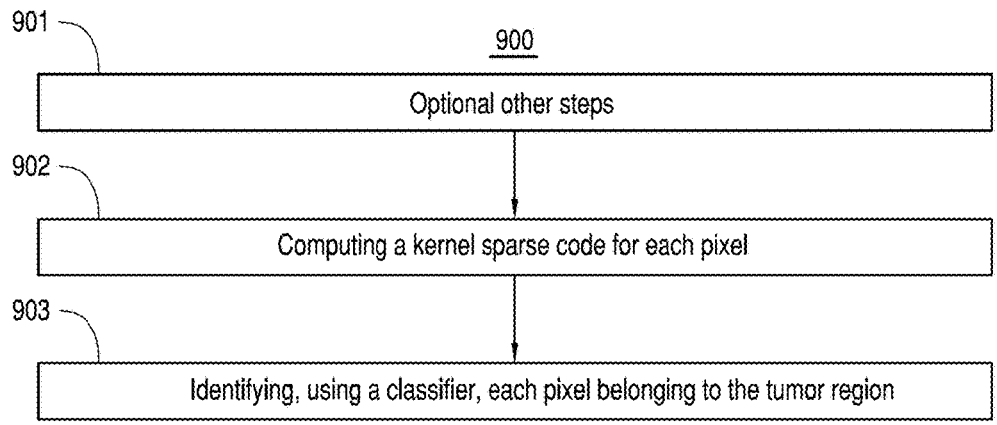
FIG. 9 illustrates a flow chart for a method of segmenting a tumor region in an image, according to an embodiment.

Turning ahead in the drawings, FIG. 9 illustrates a flow chart for a method 900 of segmenting a tumor region in an image, according to an embodiment. Method 900 is merely exemplary and is not limited to the embodiments presented herein. Method 900 can be employed in many different embodiments or examples not specifically depicted or described herein. In some embodiments, the procedures, the processes, and/or the activities of method 900 can be performed in the order presented. In other embodiments, the procedures, the processes, and/or the activities of method 900 can be performed in any suitable order. In still other embodiments, one or more of the procedures, the processes, and/or the activities of method 900 can be combined or skipped. In some embodiments, method 900 can be implemented via execution of computer instructions configured to run at one or more processing modules and configured to be stored at one or more non-transitory memory storage modules. For example, method 900 can be implemented by computer system 700 (FIG. 7).

Figure 10:
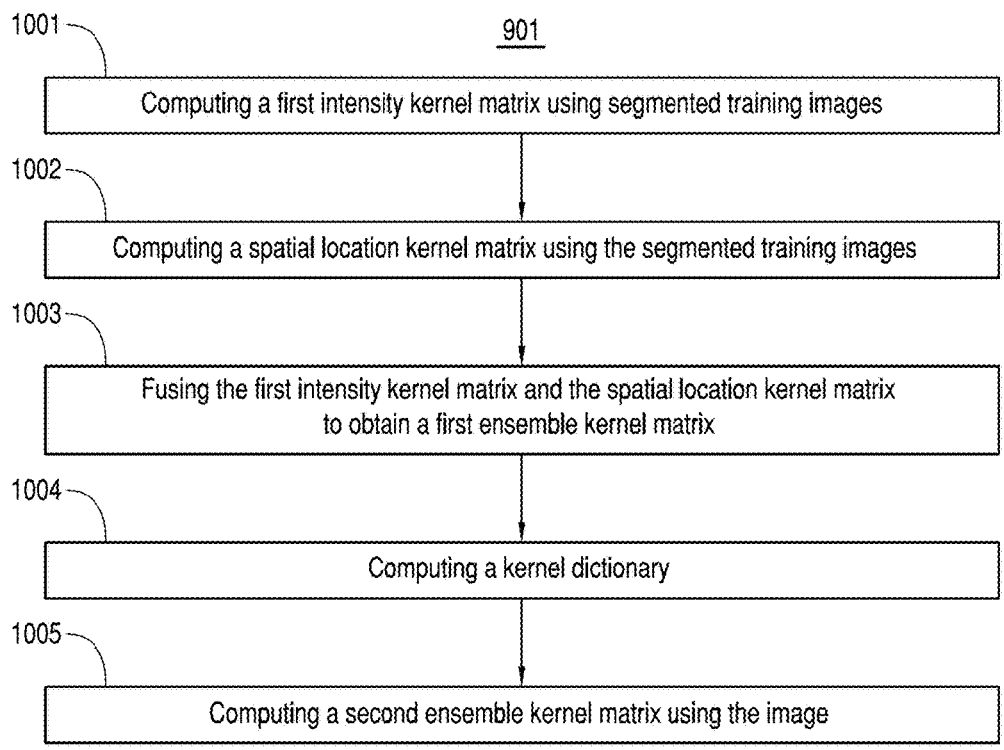
FIG. 10 illustrates a flow chart for an embodiment of optional other steps, according to the embodiment of FIG. 9.
Figure 11:
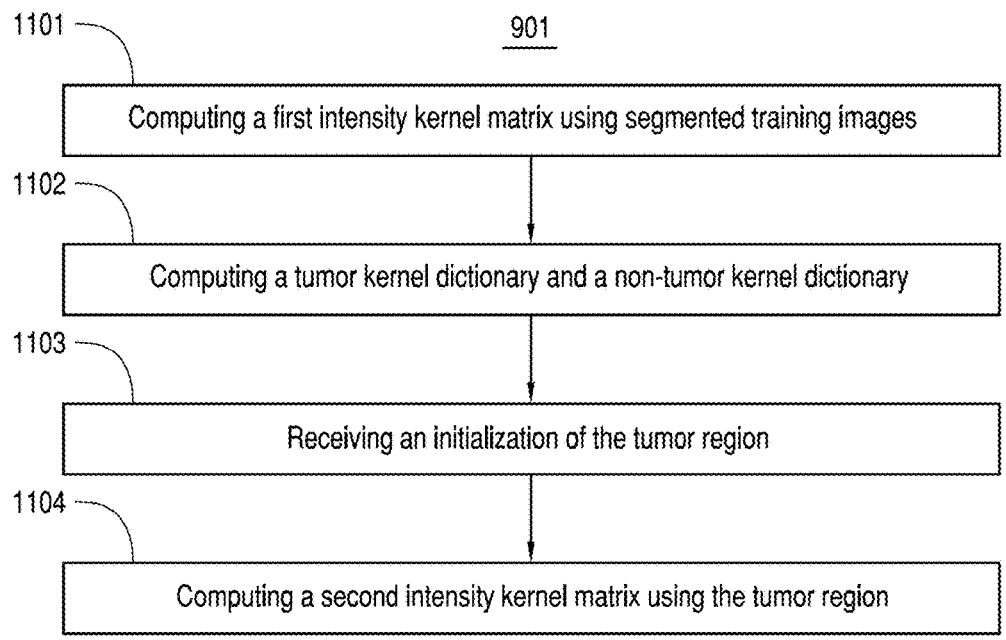
FIG. 11 illustrates a flow chart for another embodiment of optional other steps, according to the embodiment of FIG. 9.

Referring to FIG. 9, in some embodiments method 900 can include block 901 of optional other steps, as shown in FIGS. 10-11 and described below. In some embodiments, method 900 can skip block 901 of option other steps.

Method 900 also can include block 902 of computing a kernel sparse code for each pixel of at least a portion of the image. As described above, the image can be a test image. In many embodiments, the image can be a T1-weighted contrast-enhanced MRI scan. In various embodiments, the tumor region can represent at least a portion of a brain tumor. In a number of embodiments, the tumor region can represent at least a portion of a GBM tumor. In certain embodiments, one or more learned dictionaries can be computed using kernel K-lines clustering, as described above. In some embodiments, computing a kernel sparse code for each pixel can include computing the kernel sparse code for each pixel using the one or more learned dictionaries. For example, the one or more learned dictionaries can include a tumor kernel dictionary and a non-tumor kernel dictionary, as described above in the KSCSA segmentation approach. The tumor kernel dictionary and the non-tumor kernel dictionary can each be based at least in part on intensity and not on spatial location, as described above in the KSCSA segmentation approach. In other embodiments, the one or more learned dictionaries can be based at least in part on both intensity and spatial location, as described in the KCSA segmentation algorithm.

In some embodiments, for example, computing the kernel sparse code for each pixel can include computing the kernel sparse code for each pixel based at least in part on an ensemble kernel matrix computed using the image and a kernel dictionary, as described above in the KCSA segmentation algorithm. In other embodiments, computing the kernel sparse code for each pixel can include computing the kernel sparse code for each pixel in a tumor region in the image based at least in part on an ensemble kernel matrix computed using the tumor region in the image and at least one of a tumor kernel dictionary or a non-tumor kernel dictionary, as described above. For example, in some embodiments, computing the kernel sparse code for each pixel can include computing the kernel sparse code for each pixel in the tumor region based on the ensemble kernel matrix computed using the tumor region in the image and the tumor kernel dictionary, and can include computing the kernel sparse code for each pixel in the tumor region based on the ensemble kernel matrix computed using the tumor region in the image and the non-tumor kernel dictionary, as described above in the KSCSA segmentation approach.

Method 900 also can include block 903 of identifying, using a classifier, each pixel belonging to the tumor region, as described above. In certain embodiments, the classifier can be a 2-class linear classifier (e.g., SVM), as described above in the KCSA segmentation algorithm. In other embodiments, the classifier can be a reconstruction error-based classifier, as described above in the KSCSA segmentation approach. In a number of embodiments, at least a portion of the tumor region can be displayed on a screen, such as screen 708 (FIG. 7). For example, the tumor region can be displayed on screen 708 as shown in the various examples of FIG. 6. As a specific example, if the classifier is a 2-class linear SVM, as described in the KCSA segmentation algorithm, the tumor region can be displayed on screen 708 as shown in the fourth column of images (from left to right) in FIG. 6. As another example, if the classifier is a reconstruction error-based classifier, as described in the KCSCA segmentation approach, the tumor region can be displayed on screen 708 as shown in the fifth column of images (from left to right) in FIG. 6.

Turning ahead in the drawings, FIG. 10 illustrates a flow chart for an embodiment of block 901. Block 901 is merely exemplary and is not limited to the embodiments presented herein. Block 901 can be employed in many different embodiments or examples not specifically depicted or described herein. In some embodiments, the procedures, the processes, and/or the activities of block 901 can be performed in the order presented. In other embodiments, the procedures, the processes, and/or the activities of block 901 can be performed in any suitable order. In still other embodiments, one or more of the procedures, the processes, and/or the activities of block 901 can be combined or skipped.

Referring to FIG. 10, in some embodiments block 901 can include block 1001 of computing an intensity kernel matrix using segmented training images. For example, the segmented training images can be expert-segmented training images, and computing the intensity kernel matrix using the expert-segmented training images can be identical or similar as described above in the KCSA segmentation algorithm.

Block 901 also can include block 1002 of computing a spatial location kernel matrix using the segmented training images. For example, computing the spatial location kernel matrix using the segmented (e.g., expert-segmented) training images can be identical or similar as described above in the KCSA segmentation algorithm.

Block 901 also can include block 1003 of fusing the intensity kernel matrix computed in block 1001 with the spatial location kernel matrix computed in block 1002 to obtain an ensemble kernel matrix. For example, fusing the intensity kernel matrix with the spatial location kernel matrix to obtain an ensemble kernel matrix can be identical or similar as described above in the KCSA segmentation algorithm.

Block 901 also can include block 1004 of computing a kernel dictionary based at least in part on the ensemble kernel matrix fused in block 1003, as described above. In a number of embodiments, computing the kernel dictionary can be performed using kernel K-lines clustering, as described above in the KCSA segmentation algorithm.

Block 901 also can include block 1005 of computing an ensemble kernel matrix using the image. For example, computing the ensemble kernel matrix using the image can be identical or similar to computing the ensemble kernel matrix using test images as described above in the KCSA segmentation algorithm.

Turning ahead in the drawings, FIG. 11 illustrates a flow chart for another embodiment of block 901. Referring to FIG. 11, in some embodiments block 901 can include block 1101 of computing an intensity kernel matrix using segmented training images. For example, the segmented training images can be expert-segmented training images, and computing the intensity kernel matrix using the expert-segmented training images can be identical or similar as described above in the KSCSA segmentation approach.

Block 901 also can include block 1102 of computing a tumor kernel dictionary and a non-tumor kernel dictionary, as described above. In a number of embodiments, each dictionary of the tumor kernel dictionary and the non-tumor kernel dictionary can be computed using kernel K-lines clustering. In many embodiments, each dictionary of the tumor kernel dictionary and the non-tumor kernel dictionary can be based at least in part on intensity and not on spatial location, as described above in the KSCSA segmentation approach.

Block 901 also can include block 1103 of receiving an initialization of the tumor region in the image. For example, the initialization of the tumor region in the image can be identical or similar as described above in the KSCSA segmentation approach.

Block 901 also can include block 1104 of computing an intensity matrix using the tumor region in the image. For example, computing an intensity matrix using the tumor region in the image can be similar or identical as described above in the KSCSA segmentation approach.

Figure 12:
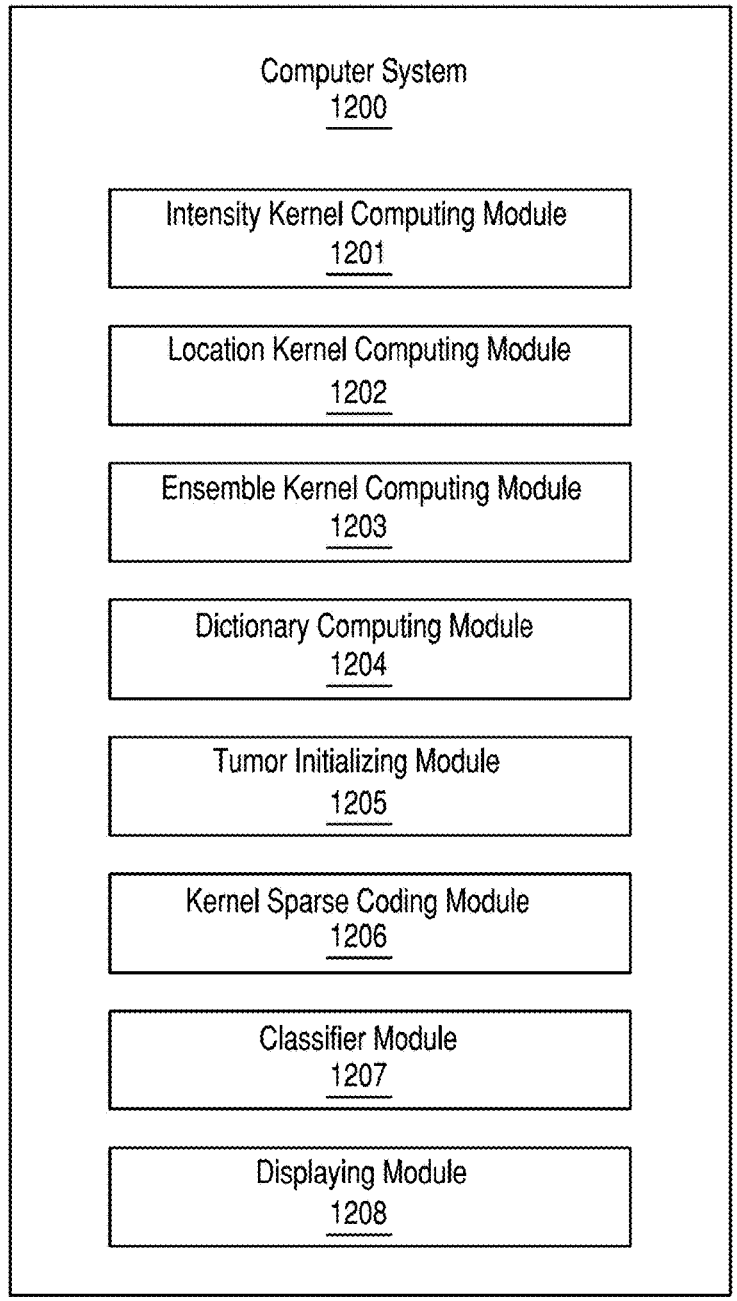
FIG. 12 illustrates a block diagram of computer system, according to another embodiment.

Turning ahead in the drawings, FIG. 12 illustrates a block diagram of computer system 1200, according to an embodiment. Computer system 1200 can be employed in many different embodiments or examples not specifically depicted or described herein. In some embodiments, certain elements or modules of computer system 1200 can perform various procedures, processes, and/or acts. In other embodiments, the procedures, processes, and/or acts can be performed by other suitable elements or modules. In some embodiments, computer system 1200 can be identical or similar to computer system 700 (FIG. 7).

In a number of embodiments, computer system 1200 can include an intensity kernel computing module 1201. In certain embodiments, intensity kernel computing module 1201 can partially or fully perform one or more of block 1001 (FIG. 10) of computing a first intensity kernel matrix using expert-segmented training images, block 1005 (FIG. 10) of computing a second ensemble kernel matrix using the image, block 1101 (FIG. 11) of computing a first intensity kernel matrix using expert-segmented training images, and/or block 1104 (FIG. 11) of computing a second intensity kernel matrix using the tumor region. In some embodiments, computer system 1200 can include a location kernel computing module 1202. In certain embodiments, location kernel computing module 1202 can partially or fully perform block 1002 (FIG. 10) of computing a spatial location kernel matrix using the expert-segmented training images.

In various embodiments, computer system 1200 can include an ensemble kernel computing module 1203. In certain embodiments, ensemble kernel computing module 1203 can partially or fully perform one or more of block 1003 (FIG. 10) of fusing the intensity kernel matrix and the spatial location kernel matrix to obtain a first ensemble kernel matrix and/or block 1005 (FIG. 10) of computing a second ensemble kernel matrix using the image. In many embodiments, computer system 1200 can include a dictionary computing module 1204. In certain embodiments, dictionary computing module 1204 can partially or fully perform one or more of block 1004 (FIG. 10) of computing a kernel dictionary and/or block 1102 (FIG. 11) of computing a tumor kernel dictionary and a non-tumor kernel dictionary.

In a number of embodiments, computer system 1200 can include a tumor initializing module 1205. In certain embodiments, tumor initializing module 1205 can partially or fully perform block 1103 (FIG. 11) of receiving an initialization of the tumor region. In some embodiments, computer system 1200 can include a kernel sparse coding module 1206. In certain embodiments, kernel sparse coding module 1206 can partially or fully perform block 902 (FIG. 9) of computing a kernel sparse code for each pixel.

In various embodiments, computer system 1200 can include a classifier module 1207. In certain embodiments, classifier module 1207 can partially or fully perform block 903 (FIG. 9) of identifying, using a classifier, each pixel belonging to the tumor region. In many embodiments, computer system 1200 can include a displaying module 1208. In certain embodiments, displaying module 1208 display at least a portion of the tumor region on a screen, such as screen 708 (FIG. 7).

Various embodiments of the subject matter described herein include various combinations of the acts, structure, components, and features described herein, shown in the drawings, or that are known in the art. Moreover, certain procedures can include acts such as manufacturing, obtaining, or providing components that perform functions described herein or in the documents that are incorporated by reference. Furthermore, various embodiments include advertising and selling products that perform functions described herein, that contain structure described herein, or that include instructions to perform functions described herein, as examples. Such products may be obtained or provided through distributors, dealers, or over the Internet, for instance. The subject matter described herein also includes various means for accomplishing the various functions or acts described herein, in the documents that are incorporated by reference, or that are apparent from the structure and acts described.

Further, as used herein, the word "or", except where indicated otherwise, does not imply that the alternatives listed are mutually exclusive. Even further, where alternatives are listed herein, it should be understood that in some embodiments, fewer alternatives may be available, or in particular embodiments, just one alternative may be available, as examples.

Although kernel sparse models for tumor segmentation has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that any element of FIGS. 1-12 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A method of segmenting a tumor region in an image, the method being implemented via execution of computer instructions configured to run at one or more processing modules and configured to be stored at one or more non-transitory memory storage modules, the method comprising:
   computing a kernel sparse code for each pixel of at least a portion of the image;
   identifying, using a classifier, each pixel belonging to the tumor region;
   computing a first intensity kernel matrix using expert-segmented training images;
   computing a spatial location kernel matrix using the expert-segmented training images; and
   fusing the first intensity kernel matrix and the spatial location kernel matrix to obtain a first ensemble kernel matrix.

2. The method of claim 1, wherein:
   the image is a T1-weighted contrast-enhanced MRI scan.

3. The method of claim 1, wherein:
   the tumor region represents at least a portion of a brain tumor.

4. The method of claim 1, wherein:
   the tumor region represents at least a portion of a GBM tumor.

5. The method of claim 1, further comprising:
   displaying at least a portion of the tumor region on a screen.

6. The method of claim 1, further comprising:
   computing one or more learned dictionaries using kernel K-lines clustering,
   wherein:
      computing the kernel sparse code for each pixel comprises computing the kernel sparse code for each pixel using the one or more learned dictionaries.

7. The method of claim 6, wherein:
   the one or more learned dictionaries comprise a tumor kernel dictionary and a non-tumor kernel dictionary.

8. A method of segmenting a tumor region in an image, the method being implemented via execution of computer instructions configured to run at one or more processing modules and configured to be stored at one or more non-transitory memory storage modules, the method comprising:
   computing a kernel sparse code for each pixel of at least a portion of the image;
   identifying, using a classifier, each pixel belonging to the tumor region; and
   computing one or more learned dictionaries using kernel K-lines clustering, wherein:
    computing the kernel sparse code for each pixel comprises computing the kernel sparse code for each pixel using the one or more learned dictionaries;
    the one or more learned dictionaries comprise a tumor kernel dictionary and a non-tumor kernel dictionary; and
    the tumor kernel dictionary and the non-tumor kernel dictionary are each based at least in part on intensity and not on spatial location.

9. A method of segmenting a tumor region in an image, the method being implemented via execution of computer instructions configured to run at one or more processing modules and configured to be stored at one or more non-transitory memory storage modules, the method comprising:
    computing a kernel sparse code for each pixel of at least a portion of the image;
    identifying, using a classifier, each pixel belonging to the tumor region; and
    computing one or more learned dictionaries using kernel K-lines clustering,
    wherein:
        computing the kernel sparse code for each pixel comprises computing the kernel sparse code for each pixel using the one or more learned dictionaries; and
        the one or more learned dictionaries are based at least in part on both intensity and spatial location.

10. The method of claim 1, wherein:
the classifier is a 2-class linear SVM.

11. The method of claim 1, further comprising:
computing a second ensemble kernel matrix using the image.

12. The method of claim 1, further comprising:
computing a kernel dictionary based at least in part on the first ensemble kernel matrix using kernel K-lines clustering; and
computing a second ensemble kernel matrix using the image,
wherein:
    computing the kernel sparse code for each pixel comprises computing the kernel sparse code for each pixel based at least in part on the second ensemble kernel matrix and the kernel dictionary; and
    the classifier is a 2-class linear SVM.

13. A method of segmenting a tumor region in an image, the method being implemented via execution of computer instructions configured to run at one or more processing modules and configured to be stored at one or more non-transitory memory storage modules, the method comprising:
    computing a kernel sparse code for each pixel of at least a portion of the image;
    identifying, using a classifier, each pixel belonging to the tumor region;
    computing a first intensity kernel matrix using expert-segmented training images;
    computing a tumor kernel dictionary and a non-tumor kernel dictionary, each based at least in part on intensity and not on spatial location, using kernel K-lines clustering;
    receiving an initialization of the tumor region in the image; and
    computing a second intensity kernel matrix using the tumor region in the image,
    wherein:
        computing the kernel sparse code for each pixel comprises computing the kernel sparse code for each pixel in the tumor region in the image based at least in part on the second intensity kernel matrix and at least one of the tumor kernel dictionary or the non-tumor kernel dictionary; and
        the classifier is a reconstruction error-based classifier.

14. A system for segmenting a tumor region in an image, the system comprising:
    one or more processing modules; and
    one or more non-transitory memory storage modules storing computing instructions configured to run on the one or more processing modules and perform the acts of:
        computing a kernel sparse code for each pixel of at least a portion of the image;
        identifying, using a classifier, each pixel belonging to the tumor region;
        computing a first intensity kernel matrix using expert-segmented training images;
        computing a spatial location kernel matrix using the expert-segmented training images;
        fusing the first intensity kernel matrix and the spatial location kernel matrix to obtain a first ensemble kernel matrix;
        computing a kernel dictionary based at least in part on the first ensemble kernel matrix using kernel K-lines clustering; and
        computing a second ensemble kernel matrix using the image,
    wherein:
        computing the kernel sparse code for each pixel comprises computing the kernel sparse code for each pixel based at least in part on the second ensemble kernel matrix and the kernel dictionary; and
        the classifier is a 2-class linear SVM.

15. The method of claim 6, wherein:
the one or more learned dictionaries are based at least in part on both intensity and spatial location.

16. The method of claim 7, wherein:
the tumor kernel dictionary and the non-tumor kernel dictionary are each based at least in part on intensity and not on spatial location.

17. The method of claim 8, wherein:
the image is a T1-weighted contrast-enhanced MRI scan.

18. The method of claim 9, wherein:
the image is a T1-weighted contrast-enhanced MRI scan.

19. The method of claim 13, wherein:
the image is a T1-weighted contrast-enhanced MRI scan.

20. The system of claim 14, wherein:
the image is a T1-weighted contrast-enhanced MRI scan.

* * * * *